United States Patent
Yen et al.

(10) Patent No.: US 9,040,174 B2
(45) Date of Patent: May 26, 2015

(54) FLUORENE COMPOUND AND ORGANIC ELECTROLUMINESCENT DEVICE USING THE SAME

(71) Applicants: Feng-Wen Yen, Hsinchu (TW); Cheng-Hao Chang, Hsinchu (TW); Hsu-Kai Chang, Hsinchu (TW); Feng-Ying Wang, Hsinchu (TW)

(72) Inventors: Feng-Wen Yen, Hsinchu (TW); Cheng-Hao Chang, Hsinchu (TW); Hsu-Kai Chang, Hsinchu (TW); Feng-Ying Wang, Hsinchu (TW)

( * ) Notice: Subject to any disclaimer, the term of this patent is extended or adjusted under 35 U.S.C. 154(b) by 404 days.

(21) Appl. No.: 13/689,767

(22) Filed: Nov. 30, 2012

(65) Prior Publication Data
US 2014/0151645 A1 Jun. 5, 2014

(51) Int. Cl.
*H01L 51/00* (2006.01)
*C07C 13/64* (2006.01)
(Continued)

(52) U.S. Cl.
CPC ............... *C07C 13/64* (2013.01); *C07D 221/18* (2013.01); *C07C 13/62* (2013.01);
(Continued)

(58) Field of Classification Search
CPC .... C07C 13/62; C07C 13/64; C07C 2103/18; C07C 2103/90; C07D 221/18; C09K 11/06; C09K 2211/1011; C09K 2211/1029; H01L 2251/308; H01L 51/0058; H01L 51/54; H01L 51/0072; H01L 51/5012; H05B 33/14
See application file for complete search history.

(56) References Cited

U.S. PATENT DOCUMENTS

2011/0073845 A1* 3/2011 Tseng et al. .................... 257/40

OTHER PUBLICATIONS

Zhou et al., Journal of Organic Chemistry, (2006), 71(18), pp. 6822-6828.*

*Primary Examiner* — Dawn L. Garrett

(57) ABSTRACT

The present invention discloses a new fluorene compound and organic EL device using the compound. The organic EL device employing the new fluorene compound as host material can lower driving voltage, prolong half-lifetime. The fluorene compound can functions as blue emitting host material of a light emitting layer and improve CIE color purity in blue emitting device. The fluorene compound are represented by the following formula(A):

formula (A)

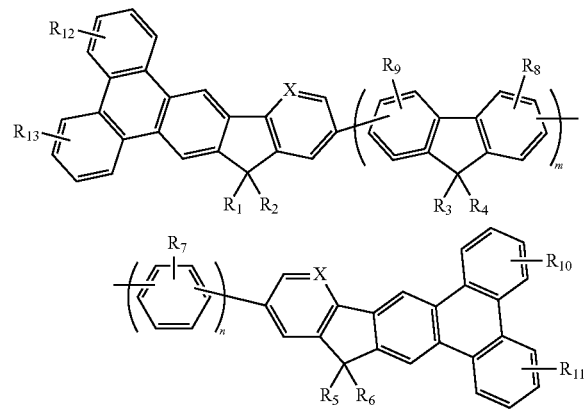

Wherein $R_1$ to $R_6$ are identical or different. $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. $R_7$~$R_{13}$ are identical or different $R_7$ to $R_{13}$ are independently selected from the group consisting of hydrogen atom, halide, alkyl group, aryl group, heteroaryl group. m and n are independently an integer of 0 to 3, X is selected from carbon or nitrogen.

7 Claims, 3 Drawing Sheets

(51) Int. Cl.
    *C07D 221/18*   (2006.01)
    *C07C 13/62*    (2006.01)
    *C09K 11/06*    (2006.01)
    *H05B 33/14*    (2006.01)
    *H01L 51/50*    (2006.01)
(52) U.S. Cl.
    CPC ........ *C07C 2103/18* (2013.01); *C07C 2103/90* (2013.01); *H01L 51/0058* (2013.01); *H01L 51/0072* (2013.01); *H01L 2251/308* (2013.01); *H01L 51/5012* (2013.01); *C09K 11/06* (2013.01); *H05B 33/14* (2013.01); *C09K 2211/1011* (2013.01); *C09K 2211/1029* (2013.01)

FLUORENE COMPOUND AND ORGANIC ELECTROLUMINESCENT DEVICE USING THE SAME

FIELD OF INVENTION

The present invention generally relates to a novel fluorene compound and organic electroluminescent (herein referred to as organic EL) device using the compound. More specifically, the present invention relates to the fluorene compound having general formula(A), an organic EL device employing the fluorene compound as fluorescence host material.

BACKGROUND OF THE INVENTION

Organic EL device has many advantages such as self-emitting, wider viewing angles, faster response speeds and highly luminescence. Their simpler fabrication and capable of giving clear display comparable with LCD, making organic EL device an industry display of choice. Organic EL device contain emissive materials which are arranged between a cathode and a anode, when a applied driving voltage is added, an electron and a hole were injected into the emissive layer and recombined to form an exciton. The exciton which results from an electron and a hole recombination have a singlet spin state or triplet spin state. Luminescence from a singlet spin state emits fluorescence and luminescence from triplet spin state emits phosphorescence.

Organic EL device are generally composed of functionally divided organic multi-layers, e.g., hole injection layer (HIL), hole transporting layer (HTL), emissive layer (EML), electron transporting layer (ETL) and electron injection layer (EIL) and so on. A emissive material have good charge carrier mobility and excellent operational durability can lower driving voltage and power consumption, Increasing efficiency and half-lifetime of Organic EL device.

For full-colored flat panel displays in AMOLED, the compounds used for the blue emissive layer are still unsatisfactory in half-lifetime and emissive colour. Many fluorene compounds are used for fluorescence blue host in emissive layer. U.S. Pat. No. 7,691,492 used 1,1'-(9,9-dimethyl-9H-fluorine-2,7-diyl)dipyrene (DFDP) as host for blue emissive electroluminescence device. U.S. Pat. No. 8,158,835 described fluorene compound used as blue, green, or red host. U.S. Pat. No. 8,110,294 also claim fluorene compound used as phosphorescence host. These compounds still have disadvantages for industrial practice use. Especially for AMOLED, except prolong half-lifetime, deep blue emission (CIE y coordinates under 0.15) is necessary for improvement.

SUMMARY OF THE INVENTION

In accordance with the present invention, the fluorene compound and their use for emissive material for Organic EL device are provided. the fluorene compound can overcome the drawbacks of the conventional materials like as shorter half-life time, lower efficiency and CIE colour purity, especially for blue fluorescent emissive material in the present invention. For full-colored flat panel displays, the blue emissive material is still not satisfied for practice use for its shorter life and CIE colour purity.

An object of the present invention is to provide the fluorene compound which can be used as emissive material for Organic EL device.

Another object of the present invention is to apply the fluorene compound for blue emissive material of Organic EL device and improve CIE colour purity & Dominate Wavelength.

Another object of the present invention is to apply the fluorene compound for blue emissive material of Organic EL device and improve the half-lifetime, lower driving voltage, lower power consumption and increase the efficiency.

The present invention has the economic advantages for industrial practice. Accordingly, the present invention discloses the fluorene compound which can be used for Organic EL device is disclosed. The mentioned the fluorene compound are represented by the following formula(A):

formula (A)

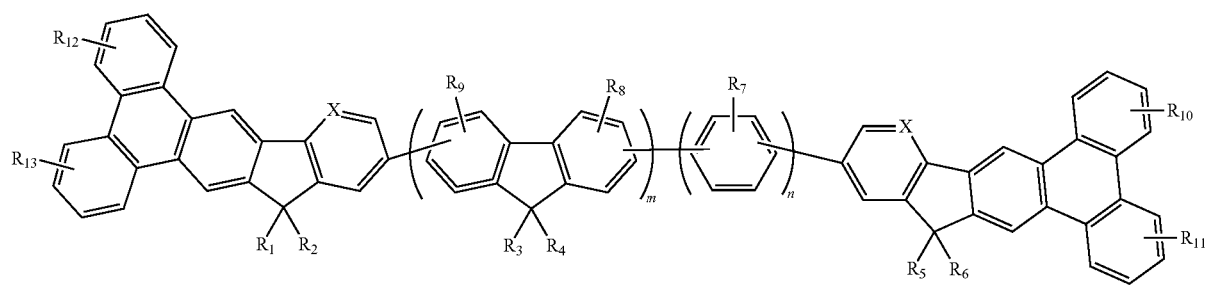

Wherein $R_1$ to $R_6$ are identical or different. $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. $R_7$~$R_{13}$ are identical or different $R_7$ to $R_{13}$ are independently selected from the group consisting of hydrogen atom, halide, alkyl group, aryl group, heteroaryl group. m and n are independently an integer of 0 to 3, X is selected from carbon or nitrogen atom.

DESCRIPTION OF THE PREFERRED EMBODIMENTS

Figure 1:
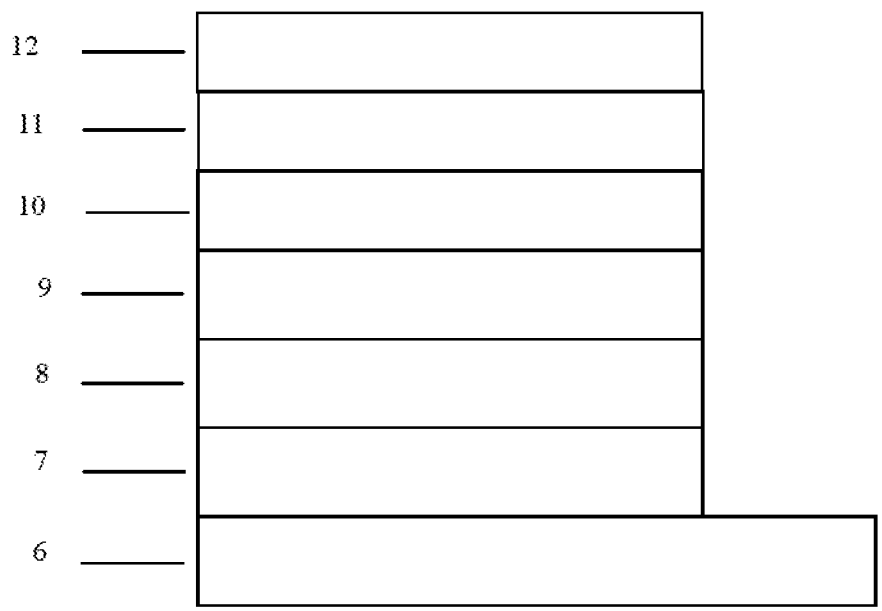
FIG. 1 show one example of organic EL device in the present invention. 6 is transparent electrode, 12 is metal electrode, 7 is hole injection layer which is deposited onto 6, 8 is hole transporting layer which is deposited onto 7, 9 is fluorescent emitting layer which is deposited onto 8, 10 is electron transporting layer which is deposited onto 9, 11 is electron injection layer which is deposited onto 10.

What probed into the invention is the fluorene compound and organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

DEFINITION

In a first embodiment of the present invention, the fluorene compound which can be used as emissive material of Organic EL device are disclosed. The mentioned fluorene compound are represented by the following formula(A):

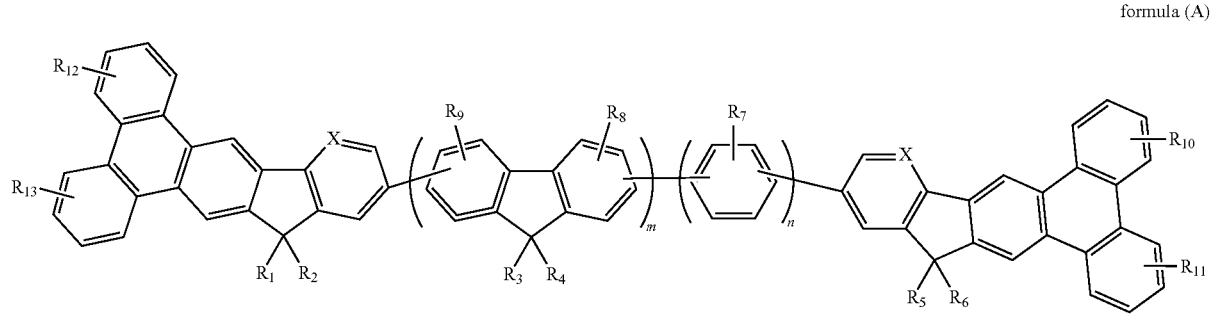

formula (A)

Wherein $R_1$ to $R_6$ are identical or different. $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. $R_7$~$R_{13}$ are identical or different $R_7$ to $R_{13}$ are independently selected from the group consisting of hydrogen atom, halide, alkyl group, aryl group, heteroaryl group. m and n are independently an integer of 0 to 3, X is selected from carbon or nitrogen atom.

In this embodiment, some fluorene compounds are shown below:

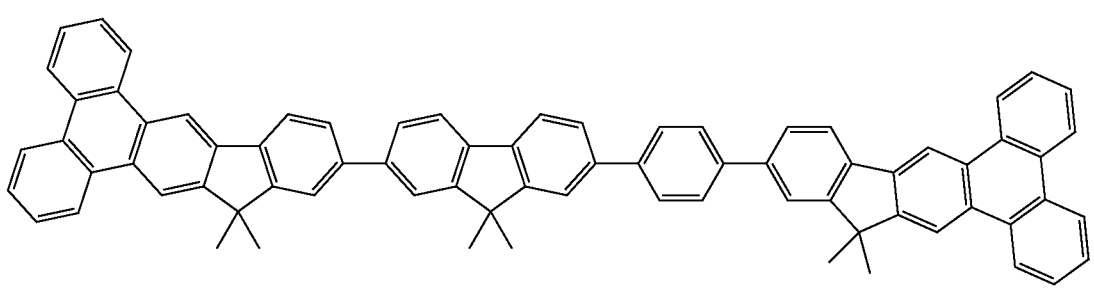

A-1

A-2
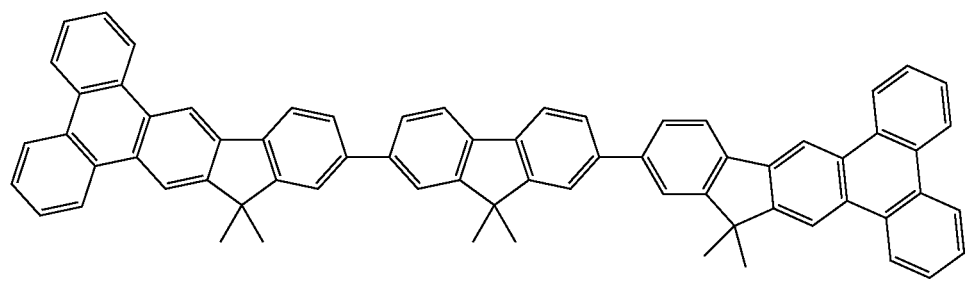
A-3
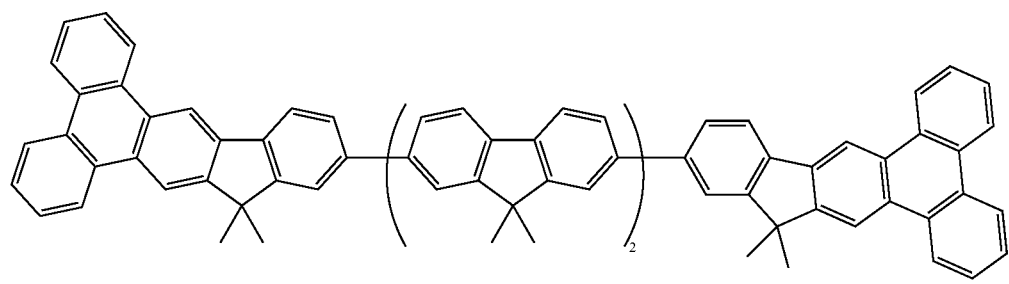
A-4
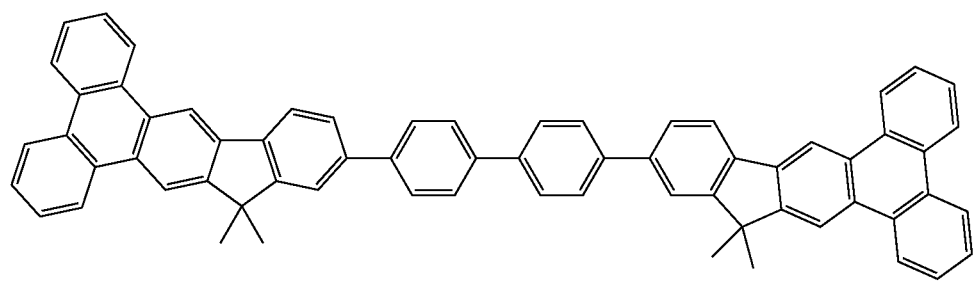
A-5
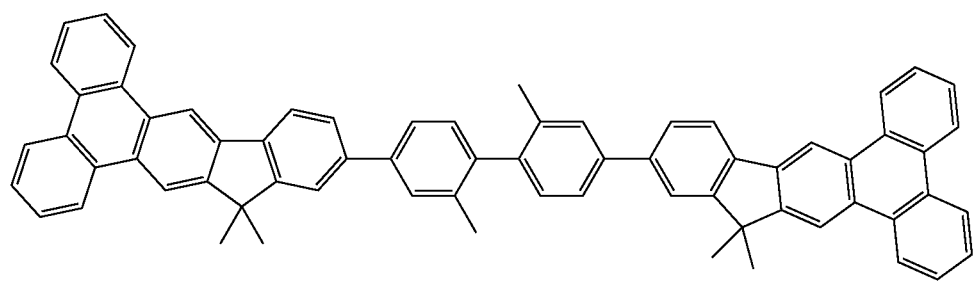
A-6
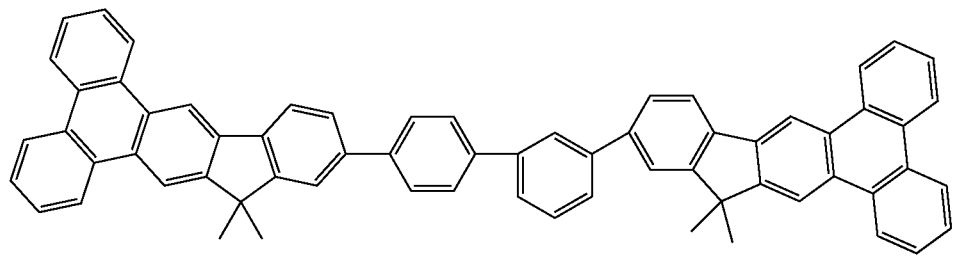

A-7
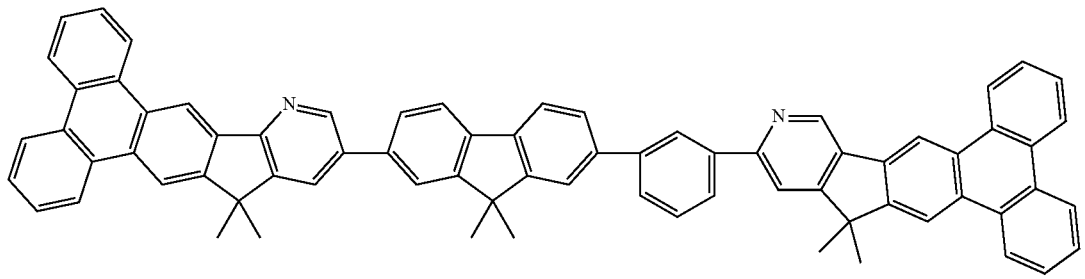
A-8
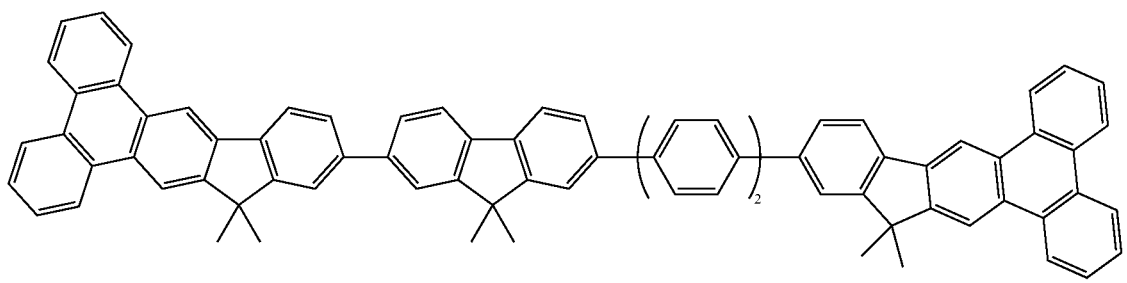
A-9
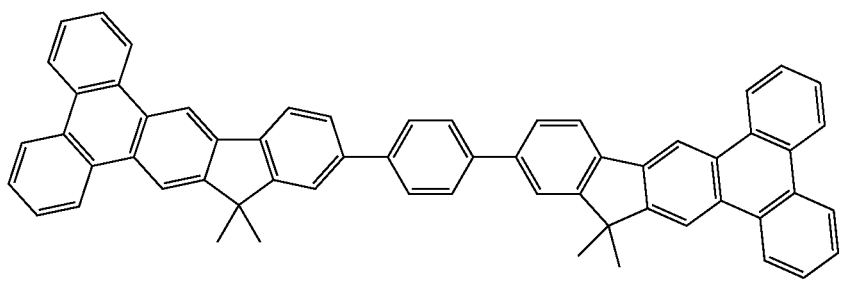
A-10
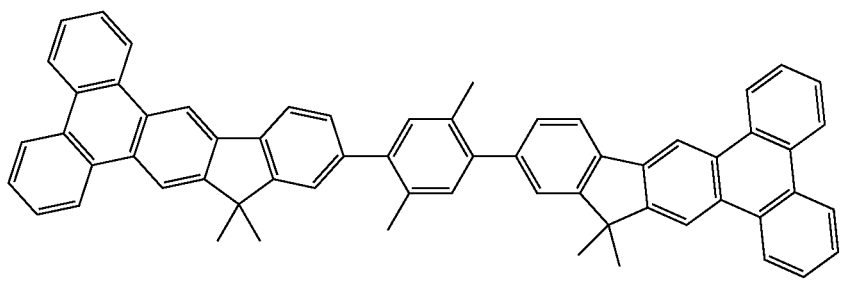
A-11
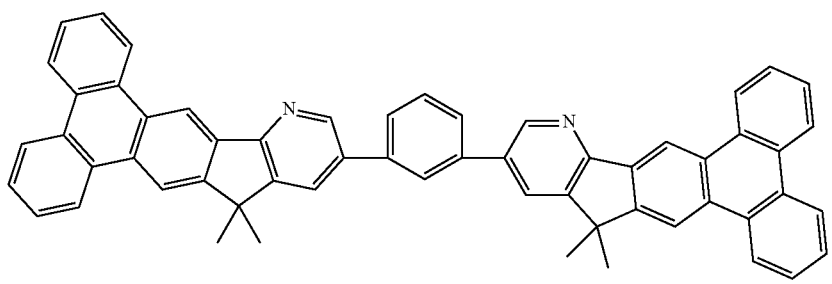

A-12

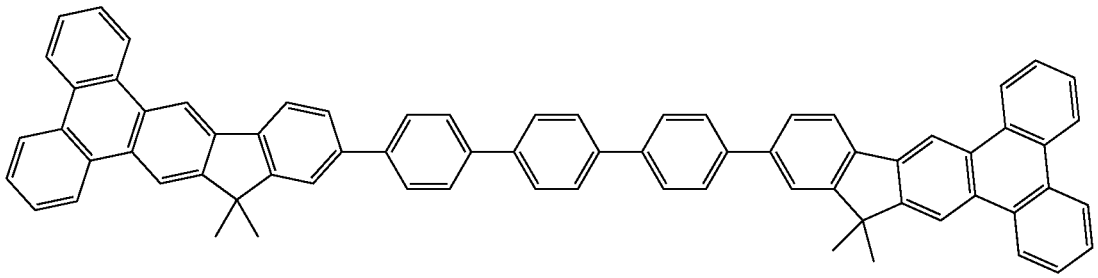

A-13

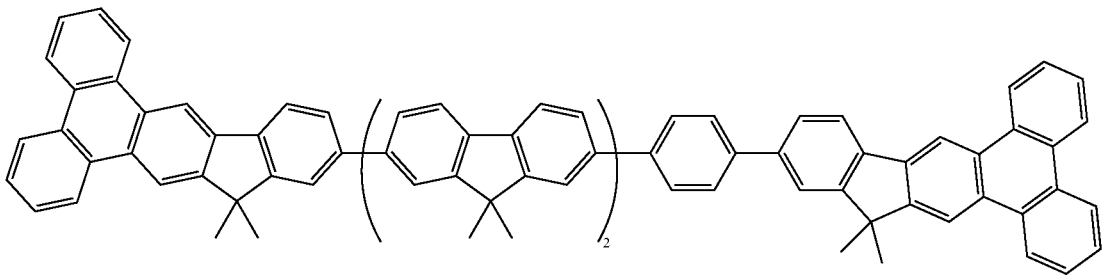

A-14

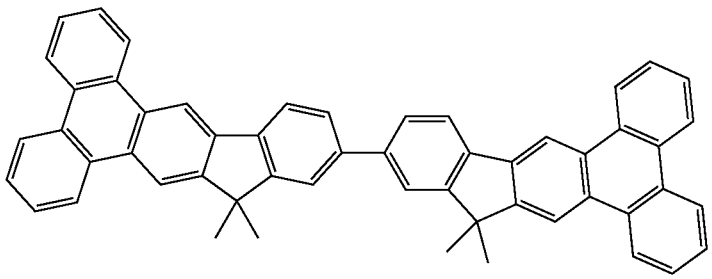

The fluorene compound for formula(A) can be prepared starting with two units of dioxaborolane substituted Indeno[2,1-b]triphenylene Suzuki coupling with dibromide substituted fluorene compounds.

Detailed preparation for formula(A) could be clarified by exemplary embodiments, but the present invention is not limited to exemplary embodiments.

Example 1

Synthesis of Compound A1

Synthesis of 2-(biphenyl-2-yl)-7-bromo-9,9-dimethyl-9H-fluorene

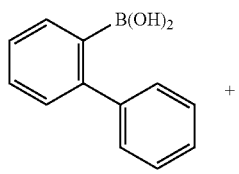
+

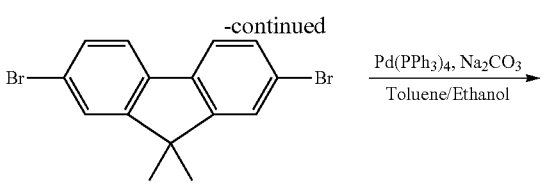

Pd(PPh3)4, Na2CO3
Toluene/Ethanol
→

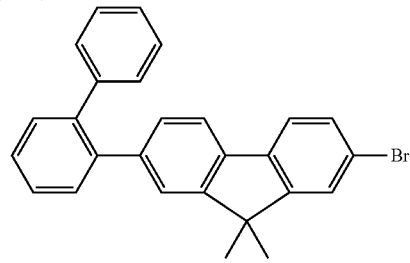

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Tetrakis(triphenylphosphine)palladium, 75 ml of 2M Na2CO3, 150 ml of EtOH and 300 ml toluene was degassed and placed under nitrogen, and then heated at 100° C. for 12 h. After finishing the reaction. The mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product (26.8 g, 63.0 mmol, 63%) as a white solid. ¹H NMR (CDCl₃, 400 MHz): δ 7.61 (d, J=7.8 Hz, 1H), 7.55~7.53 (m, 2H), 7.49~7.42 (m, 5H), 7.29 (d, J=8.0 Hz, 1H), 7.20~7.14 (m, 5H), 6.98 (s, 1H), 1.21 (s, 6H)

Synthesis of 12-bromo-10,10-dimethyl-10H-indeno[1,2-b]triphenylene

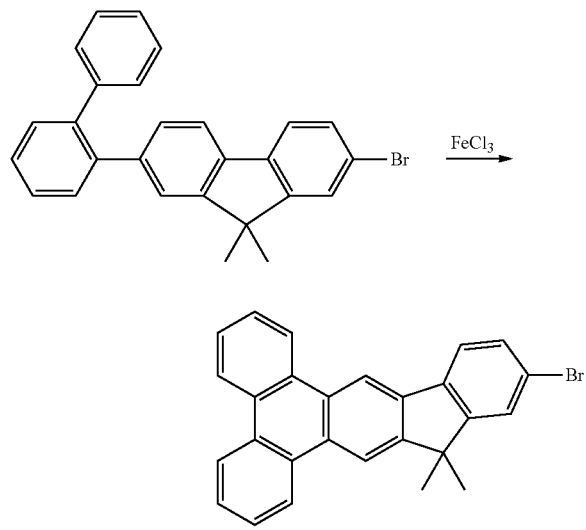

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous Dichloromethane (1500 ml), 97.5 g (600 mmol) Iron (III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). ¹H NMR (CDCl₃, 400 MHz): δ 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[1,2-b]triphenylene-12-yl)-4,4,5,5-tetramethyl-1,3,2-dioxaborolane

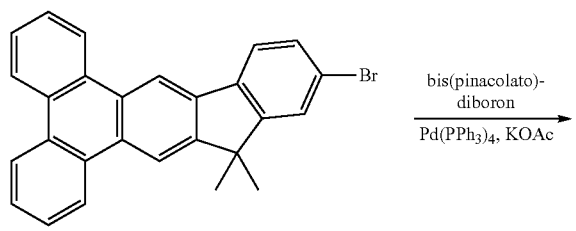

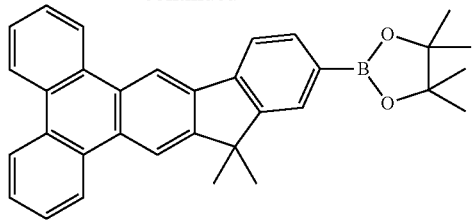

A mixture of 10.7 g (25.3 mmol) of 12-bromo-10,10-dimethyl-10H-Indeno[1,2-b]triphenylene, 7.7 g (30.3 mmol) of bis(pinacolato)diboron, 0.3 g (0.26 mmol) of Tetrakis(triphenylphosphine)palladium, 7.4 g (75.4 mmol) of potassium acetate, and 300 ml 1,4 dioxane was degassed and placed under nitrogen, and then heated at 90° C. for 16 h. After finishing the reaction. The mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid. ¹H NMR (CDCl₃, 400 MHz): δ 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of 12-(7-bromo-9,9-dimethyl-9H-fluoren-2-yl)-10,10-dimethyl-10H-indeno[2,1-b]triphenylene

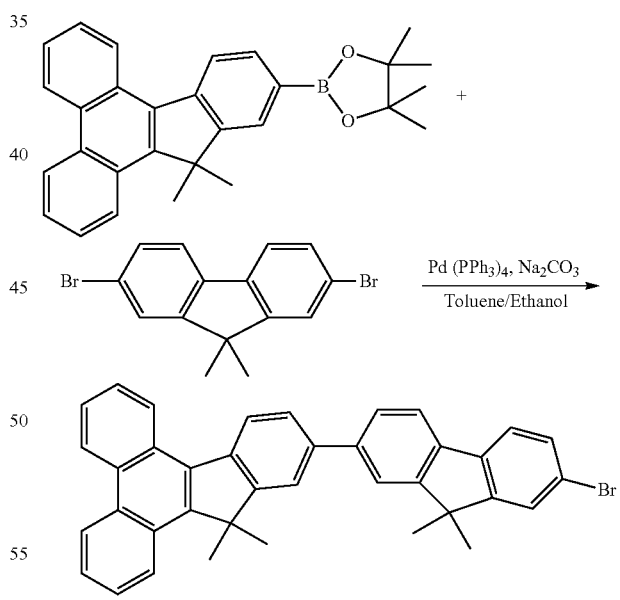

A mixture of 4.9 g (14 mmol) of 2,7-dibromo-9,9-dimethyl-9H-fluorene, 7.53 g (16 mmol) of 2-(10,10-dimethyl-10H-indeno[1,2-b]triphenylen-12-yl)-4,4,5,5-tetramethyl-1,3,2-dioxaborolane, 0.16 g (0.14 mmol) of Tetrakis(triphenylphosphine)palladium, 11 ml of 2M Na₂CO₃, 30 ml of EtOH and 65 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction. To give 3.7 g (yield 43%) of yellow product which was recrystallized from toluene.

Synthesis of 12-(4-bromophenyl)-10,10-dimethyl-10H-indeno[2,1-b]triphenylene

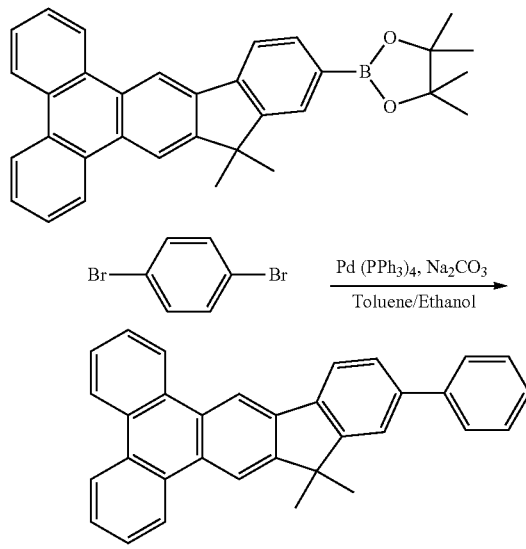

A mixture of 6.6 g (28 mmol) of 1,4-dibromobenzene, 15.1 (32 mmol) of 2-(10,10-dimethyl-10H-indeno[1,2-b]triphenylen-12-yl)-4,4,5,5-teramethyl-1,3,2-dioxaborolane, 0.32 g (0.28 mmol) of Tetrakis(triphenylphosphine)palladium, 22 ml of 2M Na₂CO₃, 60 ml of EtOH and 130 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction and the residue was purified by column chromatography on silica (hexane-dichloromethane) to give product 7.4 g (53%) as a white solid.

Synthesis of 2-(4-(10,10-dimethyl-10H-indeno[2,1-b]triphenylen-12-yl)phenyl)-4,4,5,5-tetramethyl-1,3,2-dioxaborolane

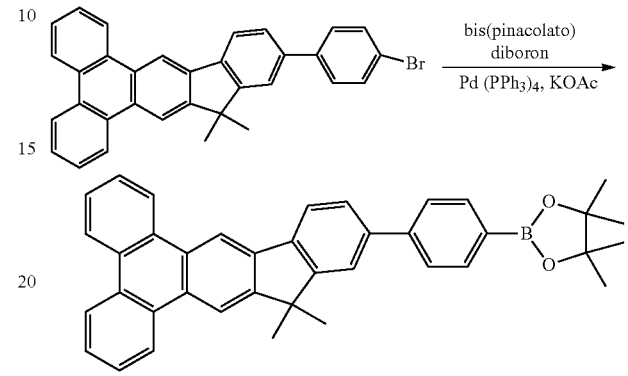

A mixture of 7.4 g (14.8 mmol) 12-(4-bromophenyl)-10,10-dimethyl-10H-indeno[2,1-b]triphenylene, 4.9 g (19.3 mmol) of bis(pinacolato)diboron, 0.17 g (0.148 mmol) of Tetrakis(triphenylphosphine)palladium, 2.9 g (29.6 mmol) of potassium acetate, and 50 ml 1,4 dioxane was degassed and placed under nitrogen, and then heated at 90° C. for 24 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (5.9 g, 73%) as a white solid.

Synthesis of 12-(4-(7-(10,10-dimethyl-10H-indeno[2,1-b]triphenylene-12-yl)-9,9-dimethyl-9H-fluoren-2-yl)phenyl)-10,10-dimethyl-10H-indeno[2,1-b]triphenylene

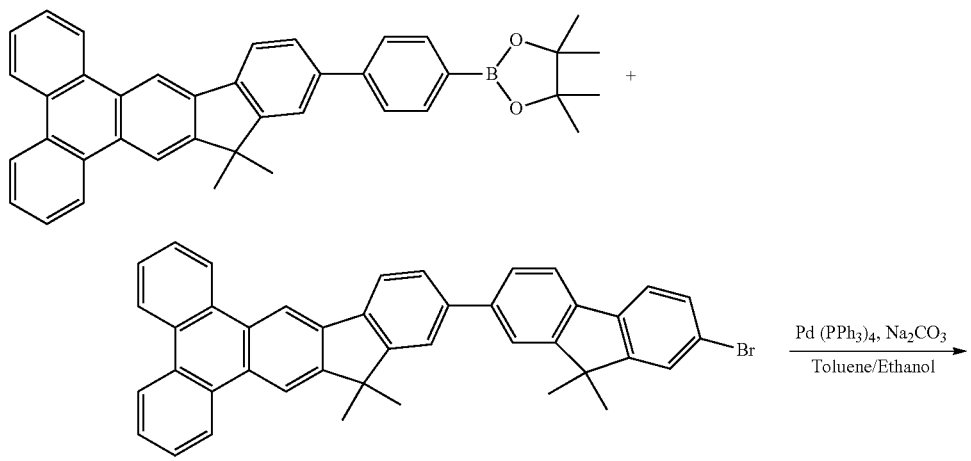

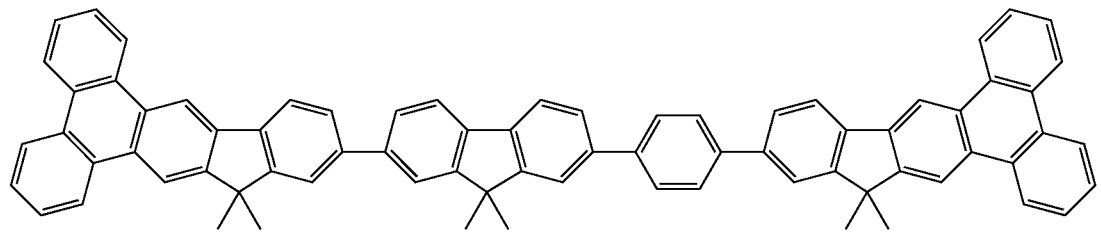

A mixture of 3.7 g (6 mmol) of 12-(7-bromo-9,9-dimethyl-9H-fluoren-2-yl)-10,10-dimethyl-10H-indeno[2,1-b]triphenylene, 3.6 g (6.6 mmol) of 2-(4-(10,10-dimethyl-10H-indeno[2,1-b]triphenylen-12-yl)phenyl)-4,4,5,5-tetramethyl-1,3,2-dioxaborolane, 0.07 g (0.06 mmol) of Tetrakis(triphenylphosphine) palladium, 6 ml of 2M $Na_2CO_3$, 15 ml of EtOH and 50 ml toluene was degassed and placed under nitrogen, and then heated at 90° C. for 24 h. After finishing the reaction. The mixture was allowed to cool to room temperature. Than 100 ml MeOH was added, while stirring and the precipitated product was filtered off with suction. To give 3.5 g (yield 61%) of yellow product which was recrystallized from chloroform. MS (m/z, $FAB^+$): 954.1 $^1$H NMR ($d_6$-DMSO, 400 MHz): δ 8.75 (s, 2H), 8.46~8.40 (m, 6H), 8.06~7.95 (m, 4H), 7.66~7.36 (m, 15H), 7.27~7.19 (m, 9H), 1.76 (s, 12H), 1.69 (s, 6H).

Example 2

Synthesis of Compound A2

Synthesis of 12,12'-(9,9-dimethyl-9H-fluorene-2,7-diyl)bis(10,10-dimethyl-10H-indeno[2,1-b]triphenylene)

A mixture of 3.52 g (10 mmol) of 2,7-dibromo-9,9-dimethyl-9H-fluorene, 10.35 g (22 mmol) of 2-(10,10-dimethyl-10H-indeno[1,2-b]triphenylen-12-yl)-4,4,5,5-tetramethyl-1,3,2-dioxaborolane, 0.12 g (0.1 mmol) of Tetrakis(triphenylphosphine)palladium, 15 ml of 2M $Na_2CO_3$, 30 ml of EtOH and 100 ml toluene was degassed and placed under nitrogen, and then heated at 90° C. for 24 h. After finishing the reaction, The mixture was allowed to cool to room temperature. Than 100 ml MeOH was added, while stirring and the precipitated product was filtered off with suction. To give 5.9 g (yield 68%) of yellow product which was recrystallized from chloroform. MS (m/z, $FAB^+$): 879.8 $^1$H NMR ($d_6$-DMSO, 400 MHz): δ 9.36 (s, 2H), 9.08 (d, J=6.0 Hz, 2H), 9.03 (s, 2H), 9.01 (d, J=6.8 Hz, 2H), 8.83 (d, J=7.2 Hz, 4H), 8.34 (d, J=6.4 Hz, 2H), 8.04 (s, 4H), 8.01 (d, J=6.4 Hz, 2H), 7.88 (d, J=6.8 Hz, 2H), 7.83 (d, J=6.0 Hz, 2H), 7.78~7.72 (m, 8H), 1.74 (s, 12H), 1.67 (s, 6H).

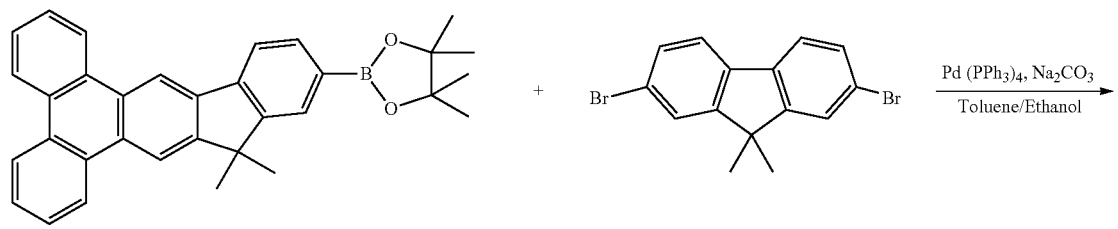

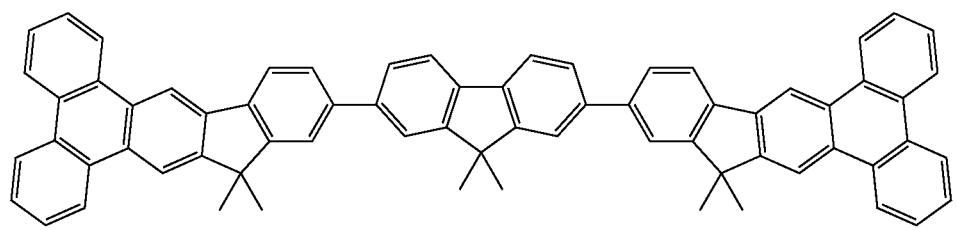

Example 3

Synthesis of Compound A10

Synthesis of 12,12'-(2,5-dimethyl-1,4-phenylene)bis(10,10-dimethyl-10H-indeno[1,2-b]triphenylene)

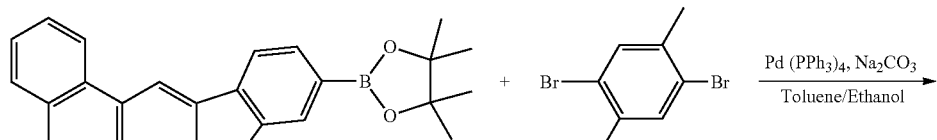

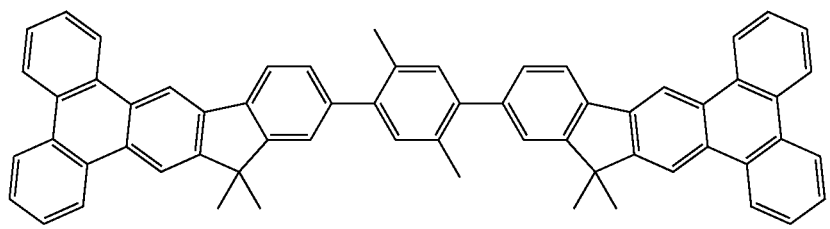

A mixture of 2.64 g (10 mmol) of 1,4-dibromo-2,5-dimethylbenzene, 10.35 g (22 mmol) of 2-(10,10-dimethyl-10H-indeno[1,2-b]triphenylen-12-yl)-4,4,5,5-tetramethyl-1,3,2-dioxaborolane, 0.12 g (0.1 mmol) of Tetrakis(triphenylphosphine)palladium, 15 ml of 2M $Na_2CO_3$, 30 ml of EtOH and 100 ml toluene was degassed and placed under nitrogen, and then heated at 90° C. for 24 h. After finishing the reaction, The mixture was allowed to cool to room temperature. Than 100 ml MeOH was added, while stirring and the precipitated product was filtered off with suction. To give 4.5 g (yield 57%) of yellow product which was recrystallized from chloroform. MS (m/z, $FAB^+$): 790.9 $^1H$ NMR ($CDCl_3$, 400 MHz): δ 9.03 (s, 2H), 8.86 (d, J=8.00 Hz, 2H), 8.76 (d, J=8.00 Hz, 2H), 8.74 (s, 2H), 8.69 (d, J=8.00 Hz, 4H), 8.10 (d, J=8.00 Hz, 2H), 7.89~7.82 (m, 6H), 7.76 (d, J=8.00 Hz, 2H), 7.74~7.67 (m, 4H), 7.21 (s, 2H), 2.75 (s, 6H), 1.75 (s, 12H).

Example 4

Synthesis of Compound A-11

Synthesis of 5H-indeno[1,2-b]pyridin-5-one

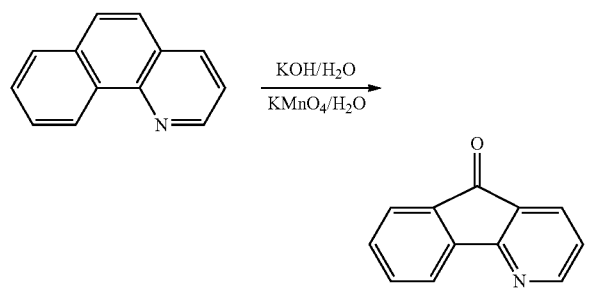

A solution of benzo[h]quinoline (6 g, 33.5 mmol) and KOH (5.6 g, 100.5 mmol) in water (400 mL) was boiled. A hot solution of $KMnO_4$ (14.8 g, 93.8 mmol) in water (240 mL) was added dropwise over 1 hour to the boiling solution. The mixture was refluxed for another 6 hours and filtered hot. The filtrate was allowed to cool to room temperature. The organic layer was extracted with chloroform and water, dried with anhydrous magnesium sulfate. After solvent removal, the residue was purified by column chromatography on silica (acetone-petroleum ether) to give product 2.5 g (42%) as a yellow solid.

Synthesis of 5H-indeno[1,2-b]pyridine

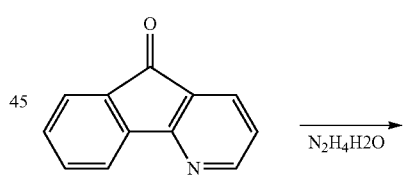

A mixture of 18.1 g (100 mmol) of 5H-indeno[1,2-b]pyridin-5-one, 27 ml (400 mmol) of hydrazine monohydrate, and 500 ml diethylene glycol was degassed and placed under nitrogen, and then heated at 170° C. for 12 h. After the reaction finish, the mixture was allowed to cool to room temperature. The organic layer was extracted with ethyl acetate and water, dried with anhydrous magnesium sulfate, the solvent was removed to give product 13.5 g (81%).

Synthesis of 5,5-dimethyl-5H-indeno[1,2-b]pyridine

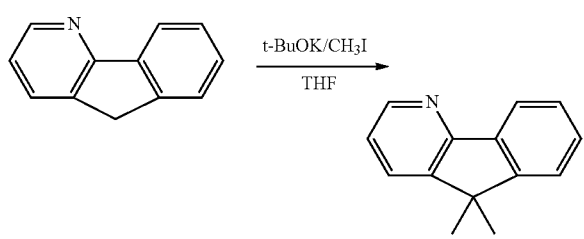

13.5 g (80.7 mmol) of 5H-indeno[1,2-b]pyridine was dissolved in 120 ml dry tetrahydrofuran, and 22.7 g (202 mmol) of potassium tert-butoxide was added to the solution at −10° C. The reaction mixture was maintained at −10° C. for 1 hour. Then the iodomethane 28.7 g (202 mmol) was added dropwise; the solution was then warmed slowly to room temperature and stirred for 6 h. After the reaction completion, water was added to the mixture to terminate the reaction. The reaction mixture was extracted with ethyl acetate and water, dried with anhydrous magnesium sulfate, the solvent was evaporated in vacuo, and the residue was crystallized with toluene to give the 5,5-dimethyl-5H-indeno[1,2-b]pyridine, 13.5 g (86%)

Synthesis of 3,7-dibromo-5,5-dimethyl-5H-indeno[1,2-b]pyridine

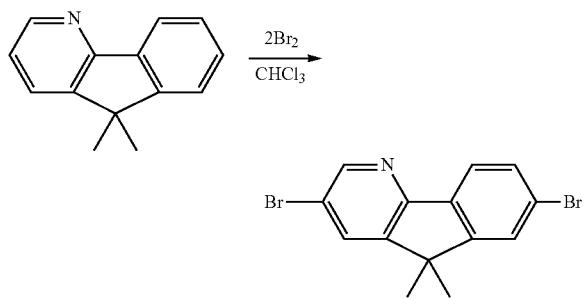

5,5-dimethyl-5H-indeno[1,2-b]pyridine (13.5 g, 69.1 mmol) was dissolved in chloroform (300 mL), protected from light and bromine (23.2 g, 145.1 mmol) diluted in chloroform (50 ml) was added dropwise. The mixture was stirred for 24 hours at room temperature, after which water (600 ml) was added, then the precipitated product was filtered off with suction, washed with MeOH and recrystallized from chloroform to give the 3,7-dibromo-5,5-dimethyl-5H-indeno[1,2-b]pyridine 13 g (53%)

Synthesis of Structural isomerism with 7-(biphenyl-2-yl)-3-Bromo-5,5-dimethyl-5H-indeno[1,2-b]pyridine and 3-(biphenyl-2-yl)-7-bromo-5,5-dimethyl-5H-indeno[1,2-b]pyridine

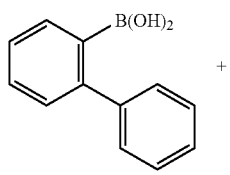

+

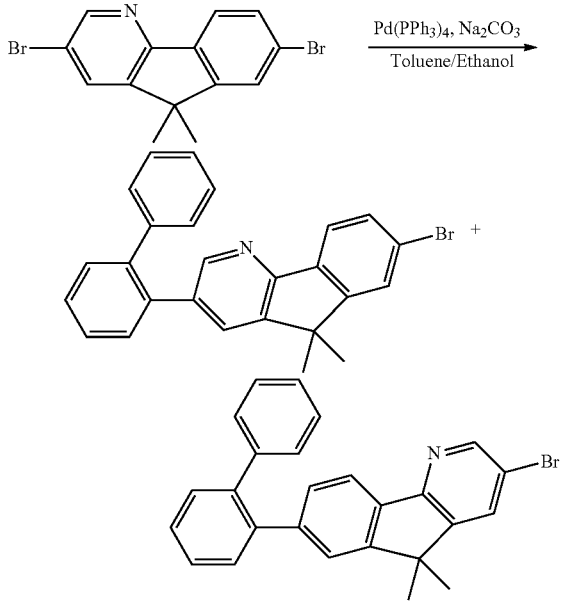

A mixture of 13 g (36.8 mmol) of 3,7-dibromo-5,5-dimethyl-5H-indeno[1,2-b]pyridine, 8.7 g (44 mmol) of biphenyl-2-ylboronic acid, 0.43 g (0.368 mmol) of Tetrakis(triphenylphosphine) Palladium, 28 ml of 2M $Na_2CO_3$, 50 ml of EtOH and 120 ml toluene was degassed and placed under nitrogen, and then heated at 90° C. for 24 h. After the reaction finish, the mixture was allowed to cool to room temperature. The organic layer was extracted with ethyl acetate and water, dried with anhydrous magnesium sulfate, the solvent was removed and the residue was washed with MeOH to give the structural isomerism product (10.4 g, 66%) which was used without further purification.

Synthesis of 12-bromo-10,10-dimethyl-10H-cyclopenta[b]pyridine[1,2-b]triphenylene and 12-bromo-10,10-dimethyl-10H-dibenzo[f,h]Indeno[1,2-b]quinoline

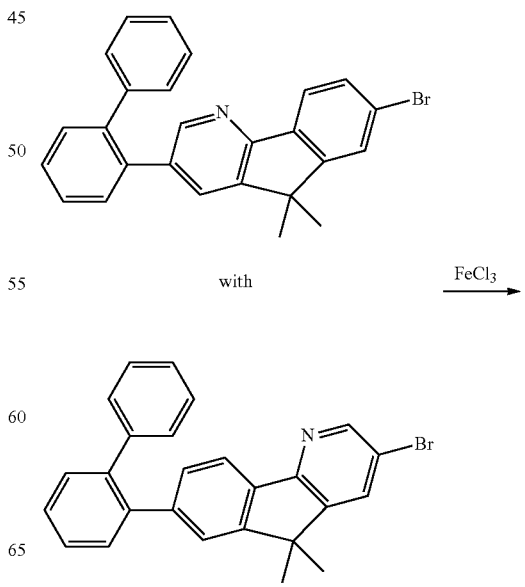

-continued

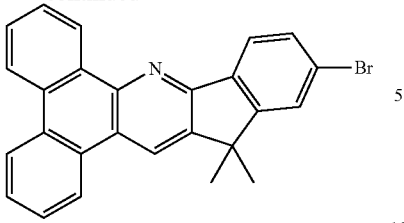

with

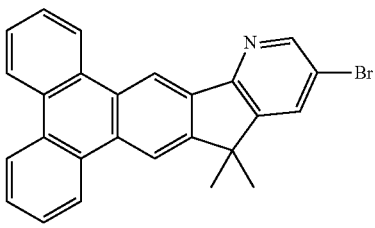

In a 2000 ml three-necked flask that had been degassed and filled with nitrogen, 10.4 g (24.4 mmol) of structural isomerism with 7-(biphenyl-2-yl)-3-bromo-5,5-dimethyl-5H-indeno[1,2-b]pyridine and 3-(biphenyl-2-yl)-7-bromo-5,5-dimethyl-5H-indeno[1,2-b]pyridine was dissolved in anhydrous dichloromethane (600 ml), 39.5 g (244 mmol) Iron(I) chloride was then added, and the mixture was stirred one hour. Methanol 500 ml were added to the mixture and the organic layer was separated and the solvent removed in vacuo. The residue was purified by column chromatography on silica (hexane-dichloromethane) to give 12-bromo-10,10-dimethyl-10H-cyclopenta[b]pyridino[1,2-b]triphenylene (1.8 g, 17.4%); $^1$H NMR (CDCl$_3$, 400 MHz): δ 9.08 (s, 1H), 8.76 (s, 1H), 8.46~8.41 (m, 2H), 8.38 (s, 14H), 8.05 (d, J=8.00 Hz, 1H), 7.96 (d, J=8.00 Hz, 1H), 7.74 (s, 1H), 7.66~7.49 (m, 4H), 1.73 (s, 6H), and 12-bromo-10,10-dimethyl-10H-dibenzo[f,h]indeno[1,2-b]quinoline (3.7 g, 35.7%); $^1$H NMR (CDCl$_3$. 400 MHz): δ 8.62~8.52 (m, 3H), 8.31 (s, 1H), 8.02 (d, J=8.00 Hz, 1H), 7.66~7.57 (m, 3H), 7.30 (t, J=8.00 Hz, 1H), 7.22 (s, 1H), 7.14~7.00 (m, 2H), 1.79 (s, 6H).

Synthesis of 4,4,5,5-tetramethyl-1,3,2-dioxaborolane-10,10-Dimethyl-10H-cyclopenta[b]pyridino[1,2-b]triphenylene

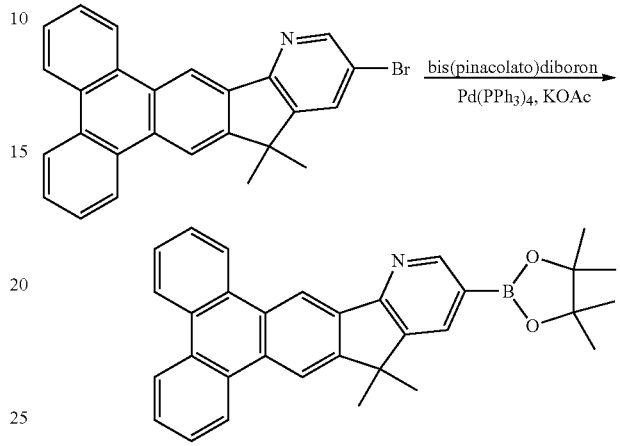

A mixture of 3 g (7 mmol) 12-bromo-10,10-dimethyl-10H-cyclopenta[b]pyridino[1,2-b]triphenylene, 2 g (7.9 mmol) of bis(pinacolato)diboron, 0.085 g (0.07 mmol) of Tetrakis(triphenylphosphine) Palladium, 2 g (21 mmol) of potassium acetate, and 50 ml 1,4 dioxane was degassed and placed under nitrogen, and then heated at 90° C. for 8 h. After the reaction finish, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (2.65 g, 80%) as a light-yellow solid.

Synthesis of 1,3-Bis(10,10-dimethyl-10H-indeno[2,1-b]triphenylen-8-yl)benzene

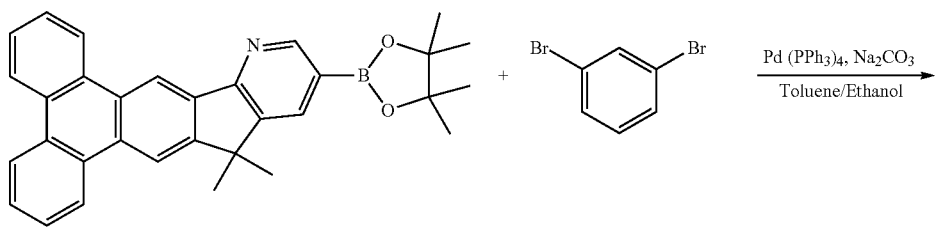

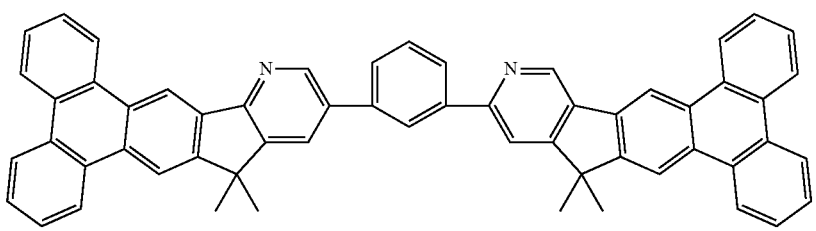

A mixture of 2.36 g (10 mmol) of 1,3-dibromobenzene, 10.37 g (22 mmol) of 4,4,5,5-tetramethyl-1,3,2-dioxaborolane-10,10-dimethyl-10H-cyclopenta[b]pyridino[1,2-b]triphenylene, 0.12 g (0.1 mmol) of tetrakis(triphenylphosphine) palladium, 15 ml of 2M $Na_2CO_3$, 30 ml of EtOH and 100 ml toluene was degassed and placed under nitrogen, and then heated at 90° C. for 24 h. After finishing the reaction, the mixture was allowed to cool to room temperature. Than 100 ml MeOH was added, while stirring and the precipitated product was filtered off with suction. To give 5.2 g (yield 68%) of yellow product which was recrystallized from chloroform. MS (m/z, FAB$^+$): 764.8 $^1$H NMR (CDCl$_3$, 400 MHz): δ 9.56 (s, 1H), 8.89 (s, 2H), 8.80 (s, 2H), 8.53 (s, 2H), 8.46~8.41 (m, 4H), 8.06~7.90 (m, 5H), 7.66~7.49 (m, 8H), 7.26 (d, 2H), 7.07 (s, 2H), 1.77 (s, 12H).

Example 5

Synthesis of Compound A14

Synthesis of 10,10,10',10'-tetramethyl-10H,10'H-12,12'-biindeno[1,2-b]triphenylene

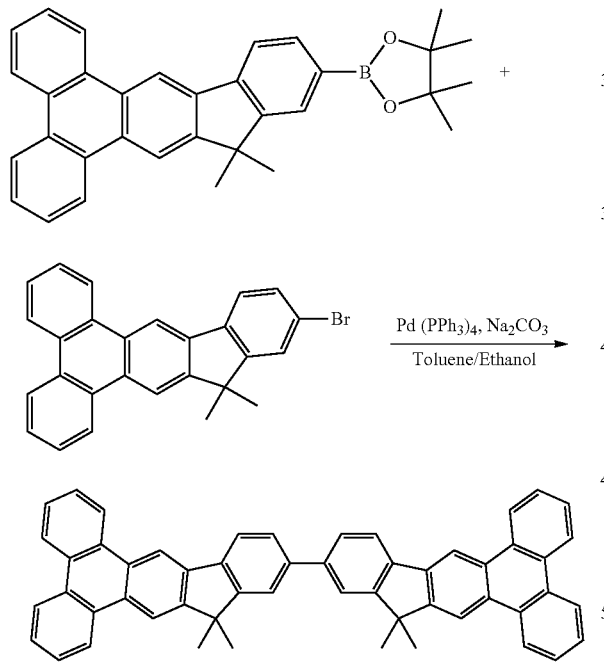

A mixture of 4.2 g (10 mmol) of 12-bromo-10,10-dimethyl-10H-indeno[1,2-b]triphenylene, 5.2 g (11 mmol) of 2-(10,10-dimethyl-10H-indeno[1,2-b]triphenylen-12-yl)-4,4,5,5-tetramethyl-1,3,2-dioxaborolane, 0.12 g (0.1 mmol) of Tetrakis(triphenylphosphine)Palladium, 15 ml of 2M Na$_2$CO$_3$, 30 ml of EtOH and 100 ml toluene was degassed and placed under nitrogen, and then heated at 90° C. for 24 h. After finishing the reaction, The mixture was allowed to cool to room temperature. Than 100 ml MeOH was added, while stirring and the precipitated product was filtered off with suction. To give 3.3 g (yield 49%) of yellow product which was recrystallized from chloroform. MS (m/z, EI): 686.7. $^1$H NMR (CDCl$_3$, 400 MHz): δ 9.05 (s, 2H), 8.86 (d, J=7.88 Hz, 2H), 8.79 (d, J=7.76 Hz, 2H), 8.74 (s, 2H), 8.71 (d, J=7.84 Hz, 4H), 8.10 (d, J=7.64 Hz, 2H), 7.84 (s, 2H), 7.81 (d, J=7.80 Hz, 2H), 7.76~7.67 (m, 8H), 1.77 (s, 12H).

General Method of Producing OLEDS

ITO-coated glasses with 12 Ω□$^{-1}$ in Resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100)

These organic layers are applied onto the ITO substrate in order by vapor deposition in a high-vacuum unit (10$^{-6}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f:2',3'-h]quinoxaline-2,3,6,7,10,11-hexacarbonitrile (Hat-CN) is used as hole injection layer in this OLEDs. N,N-Bis(naphthalene-1-yl)-N,N'-bis(phenyl)-benzidine (NPB) is most widely used as the hole transporting layer and 2,9-bis(naphthalene-2-yl)-4,7-diphenyl-1,10-phenanthroline(NBphen) is used as electron transporting material in OLEDs for its high thermal stability and long life-time than BPhen/BCP. 9,10-di(naphtha-2-yl)anthrance (AND) and 1,1'-(9,9-dimethyl-9H-fluorene-2,7-diyl) dipyrene (DFDP) is used as emissive host and (E)-6-(4-(diphenylamino)styryl)-N,N-diphenylnaphthalen-2-amine (DPASN) is used as guest. The above OLED materials for producing standard OLEDs in this invention shown its chemical structure as following:

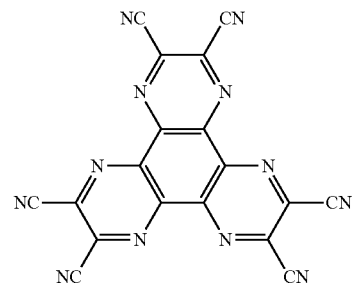

HAT-CN

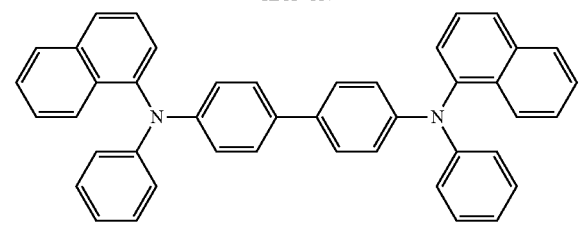

NPB

-continued

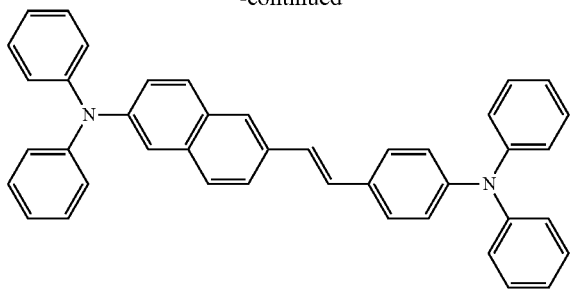

DPASN

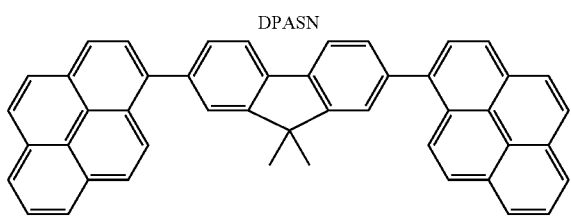

DFDP

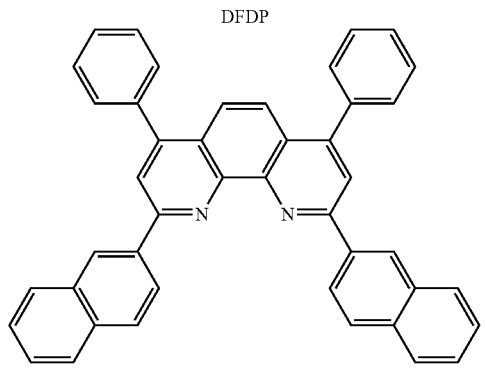

NBphen

A typical OLED consists of low work function metals, such as Al, Mg, Ca, Li and K, as the cathode by thermal evaporation, and the low work function metals can help electrons injecting the electron transporting layer from cathode. In addition, for reducing the electron injection barrier and improving the OLED performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the OLEDs fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the abovementioned general method, fluorescent blue-emitting OLEDs having the following device structure were produced (See FIG. 1): ITO/HAT-CN (200Å)/NPB (500Å)/fluorescent blue host doped 5% DPASN (300Å)/NPhen (300Å)/LiF (5Å)/Al (1600Å). The I-V-B and half-life time of fluorescent blue-emitting OLED device testing report as Table 1. The half-lifetime is defined that the initial luminance of 3000 cd/m² has dropped to half.

TABLE 1

| fluorescent blue host | Voltage (V) | Luminance (cd/m²) | Yield (cd/A) | CIE (y) | Half-lifetime(hr) Initial luminance = 3000(cd/m²) |
|---|---|---|---|---|---|
| Compound A-1 | 6 | 975 | 4.78 | 0.169 | 345 |
| Compound A-2 | 6 | 1030 | 4.33 | 0.161 | 387 |
| Compound A-10 | 6 | 601 | 2.41 | 0.118 | 160 |
| Compound A-11 | 6 | 1210 | 2.40 | 0.132 | 105 |
| Compound A-14 | 6 | 928 | 2.52 | 0.121 | 185 |
| DFDP | 6 | 1050 | 4.12 | 0.190 | 256 |

Figure 2:
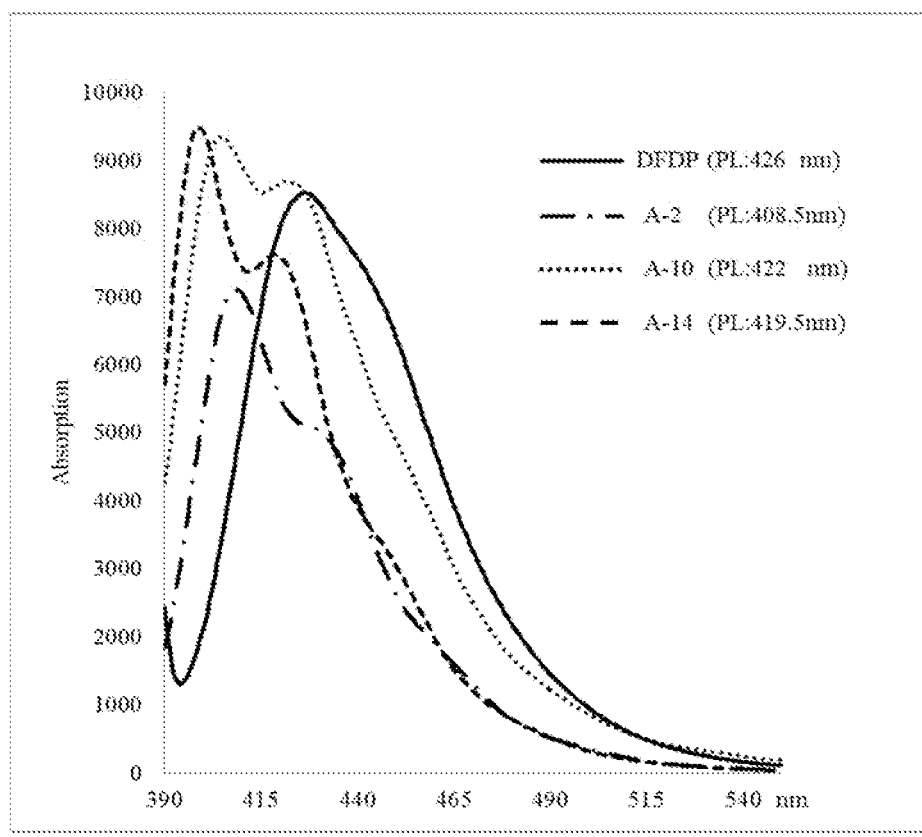
FIG. 2 show the figure of photoluminescence ((herein referred to as PL) for compound A-2, A-10 and A14 comparable with DFDP.
Figure 3:
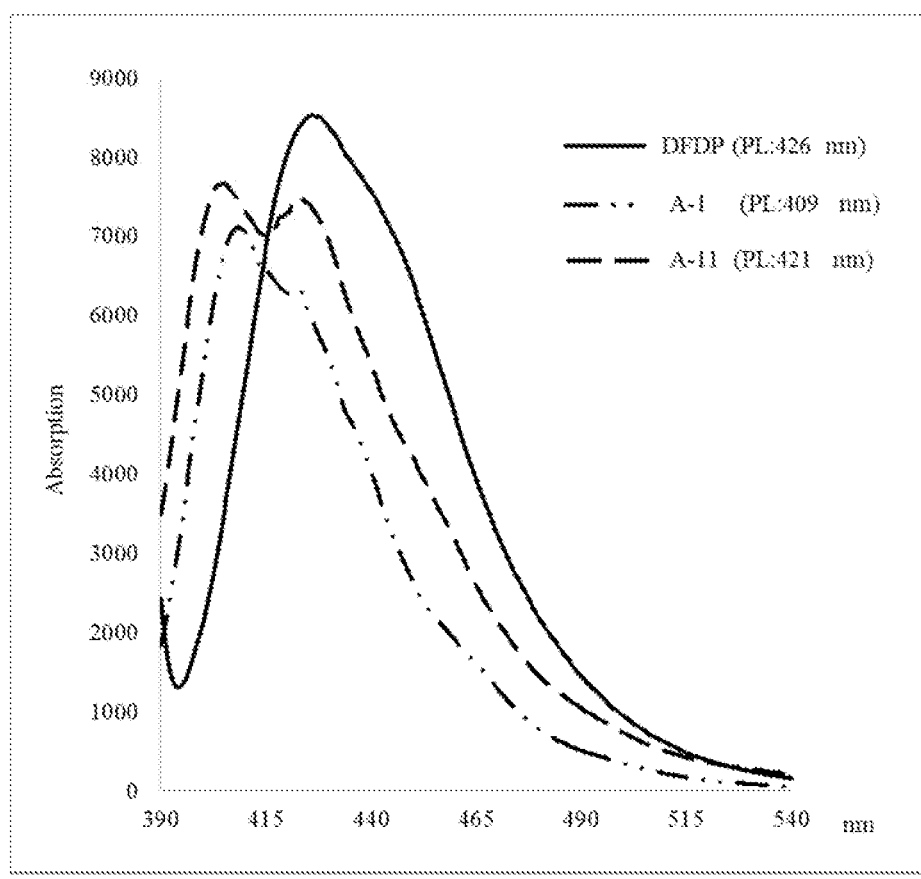
FIG. 3 show the PL figure of compound A-1 and A11 comparable with DFDP.

In the above preferred embodiments, we show that the fluorene compound of the present invention used as fluorescent blue host than comparable example DFDP with deep-blue colour coordinates and longer half-lifetime for some examples. The PL for the fluorene compounds of the present invention show blue shift than the prior art (DFDP) from FIG. 2~FIG. 3. It's also consistently with CIE(y) from Table 1.

To sum up, the present invention discloses a fluorene compound which can be used for organic EL device is disclosed. The mentioned fluorene compound are represented by the following formula(A).

formula (A)

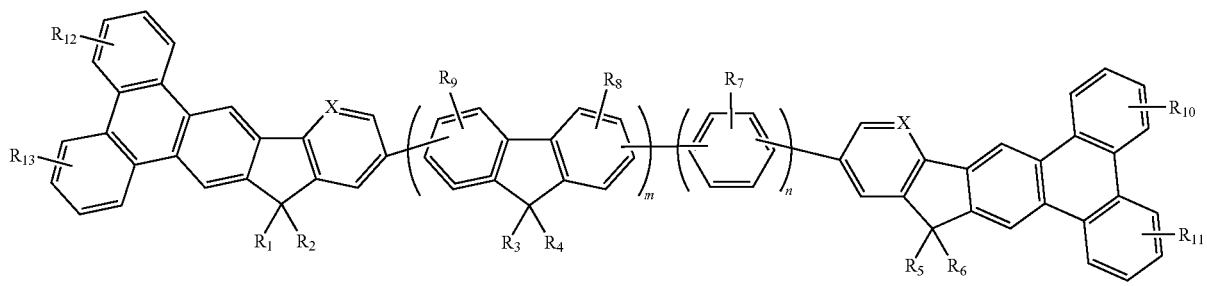

Wherein $R_1$ to $R_6$ are identical or different. $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. $R_7$~$R_{13}$ are identical or different $R_7$ to $R_{13}$ are independently selected from the group consisting of hydrogen atom, halide, alkyl group, aryl group, heteroaryl group. m and n are independently an integer of 0 to 3, X is selected from carbon or nitrogen atom.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A fluorene compound with a general formula(A) as follows:

formula (A)

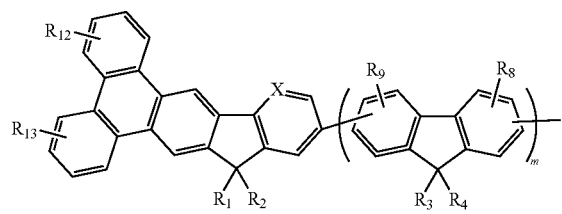

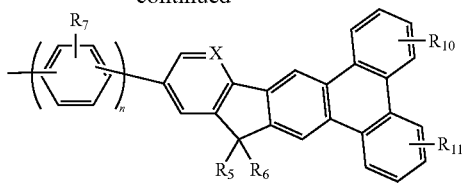

wherein $R_1$ to $R_6$ are identical or different, $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms; $R_7$~$R_{13}$ are identical or different, $R_7$ to $R_{13}$ are independently selected from the group consisting of hydrogen atom, halide, alkyl group, aryl group, and heteroaryl group; m and n are independently an integer of 0 to 3, X is selected from carbon or nitrogen.

2. The compound as claimed in claim 1, wherein X is carbon atoms and the fluorene compound is represented by the following formula (aI):

formula (aI)

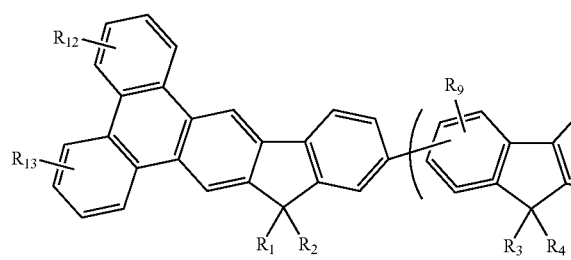

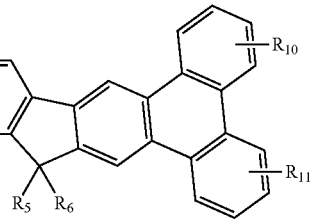

wherein $R_1$ to $R_6$ are identical or different, $R_1$ to $R_6$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms; $R_7$~$R_{13}$ are identical or different, $R_7$ to $R_{13}$ are independently selected from the group consisting of hydrogen atom, halide, alkyl group, aryl group, and heteroaryl group; m and n are independently an integer of 0 to 3.

3. The compound as claimed in claim 1, wherein X is nitrogen atom, and the fluorene compound is represented by the following formula(aII):

formula (aII)

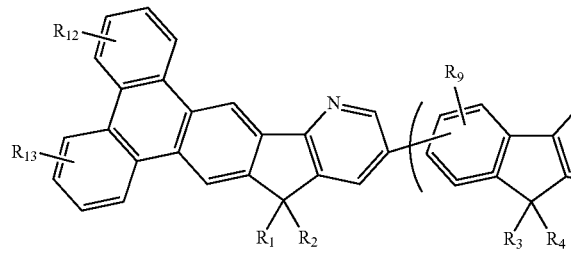

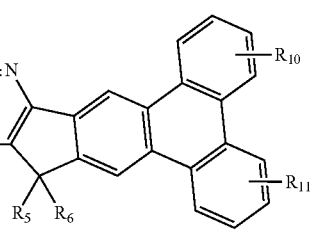

wherein R₁ to R₆ are identical or different, R₁ to R₆ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms; R₇~R₁₃ are identical or different, R₇ to R₁₃ are independently selected from the group consisting of hydrogen atom, halide, alkyl group, aryl group, and heteroaryl group; m and n are independently an integer of 0 to 3.

4. A organic EL device comprising a pair of electrodes consisting of a cathode and an anode and between the pairs of electrodes comprising a layer of fluorene compound with a general formula(A) as follows:

formula (A)

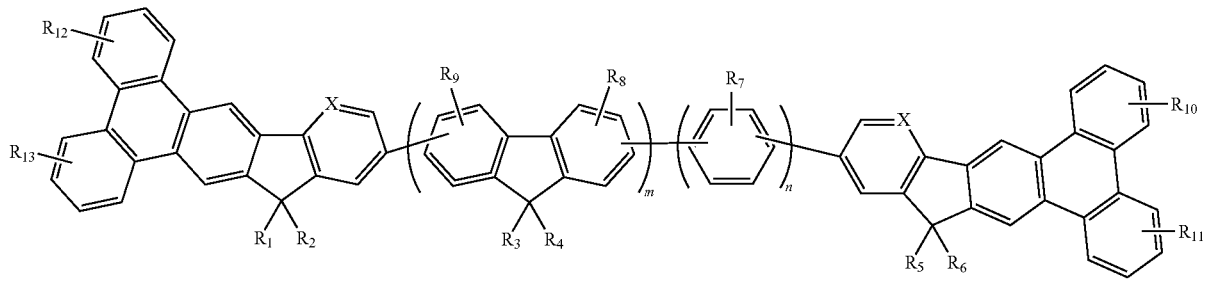

wherein R₁ to R₆ are identical or different, R₁ to R₆ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 6 to 30 carbon atoms; R₇~R₁₃ are identical or different, R₇ to R₁₃ are independently selected from the group consisting of hydrogen atom, halide, alkyl group, aryl group, and heteroaryl group; m and n are in dependently an integer of 0 to 3, X is selected from carbon or nitrogen.

5. An organic EL device according to claim 4 comprising a layer of fluorene compound which functions as host material of a light emitting layer.

6. An organic EL device according to claim 5 comprising a layer of fluorene compound which functions as blue emitting host material of a light emitting layer.

7. The fluorene compound according to claim 1, wherein the fluorene compound is selected from the group consisting of:

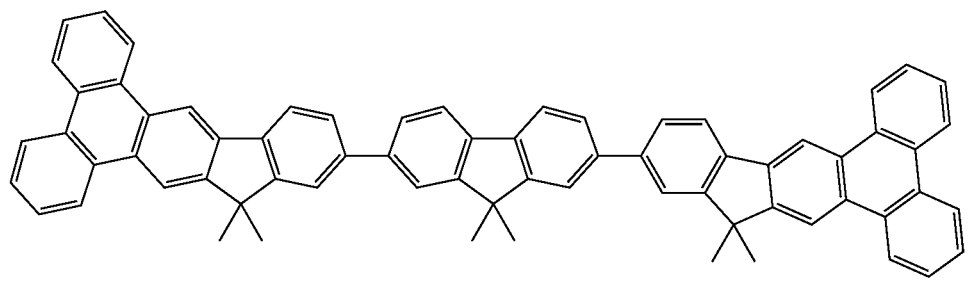

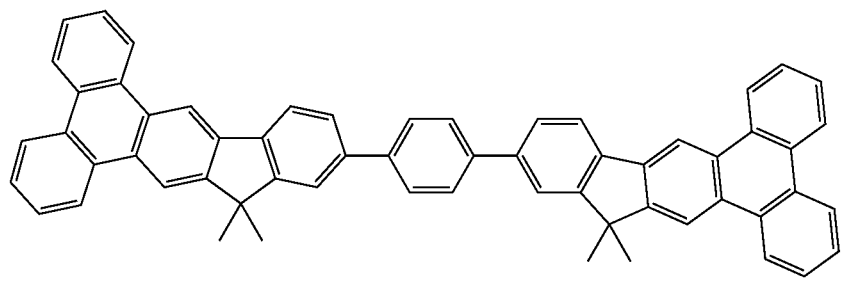

-continued
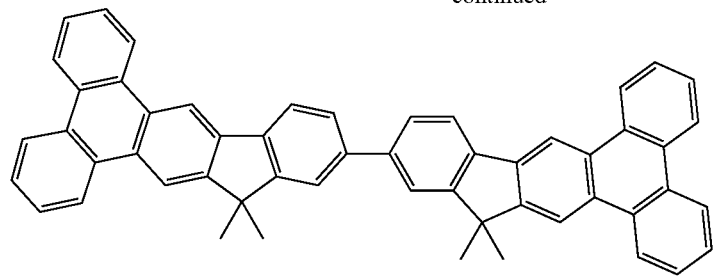
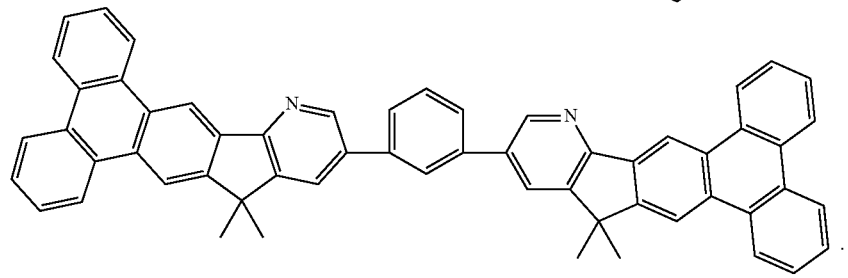
* * * * *